US00PP37290P2

(12) United States Plant Patent
Hansen

(10) Patent No.: US PP37,290 P2
(45) Date of Patent: Feb. 24, 2026

(54) ***SALVIA* PLANT NAMED 'Big Sky'**

(50) Latin Name: ***Salvia* hybrid**
Varietal Denomination: Big Sky

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,337

(22) Filed: Nov. 22, 2024

(51) Int. Cl.
*A01H 5/02* (2018.01)
*A01H 5/12* (2018.01)
*A01H 6/50* (2018.01)

(52) U.S. Cl.
USPC ..... Plt./475
CPC ..... *A01H 6/508* (2018.05); *A01H 5/02* (2013.01); *A01H 5/12* (2013.01)

(58) Field of Classification Search
USPC ..... Plt./475
See application file for complete search history.

*Primary Examiner* — Susan McCormick Ewoldt
*Assistant Examiner* — Zachariah Allan Kay

(57) ABSTRACT

The new and distinct cultivar of perennial *Salvia* plant named 'Big Sky' characterized by its large, mounded, vigorous, and winter-hardy habit. The large violet-blue flowers densely arranged in verticils on tall heavily-branched panicles that repeat if deadheaded above a mound of large, rugose, dark-green foliage. The new plant flowers without vernalization. 'Big Sky' is useful for landscaping as a specimen plant or en masse.

2 Drawing Sheets

Botanical denomination: *Salvia* hybrid.
Cultivar designation: 'Big Sky'.

STATEMENT REGARDING PRIOR DISCLOSURES UNDER 37 CFR 1.77(B)(6)

The first public disclosure and offer for sale of the new plant, in the form of a photograph and brief description on a website operated by Walters Gardens, Inc. on Dec. 1, 2023. Subsequently, the new plant was advertised in the "Walters Gardens 2024-2025 Catalog" first distributed on May 23, 2024. Walters Gardens, Inc. obtained the plant and all information relating thereto from the inventor. No plants of *Salvia* 'Big Sky' have been sold in this country or anywhere in the world, nor has any disclosure of the new plant been made, more than one year prior to the filing date of this application, and such sale or disclosure would be a 35 U.S.C. § 102(b) exception.

BACKGROUND OF THE INVENTION

The present invention relates to a new and distinct cultivar of ornamental sage plant hereinafter referred to by the cultivar name *Salvia* 'Big Sky' or as the new plant. The new plant was a single seedling selection from a cross between the proprietary, unnamed, hybrid known only as 18-25-1 (not patented) as the female or seed parent and the proprietary, unnamed, hybrid known only as 18-30-1 (not patented) as the male parent at a wholesale perennial nursery in Zeeland, Michigan, USA. The cross was performed on Jul. 10, 2019, the seed was collected in the summer of 2019, and sown at the same nursery. The new plant was initially evaluated in the summer of 2020 and assigned the breeder code 19-30-7 through the trial process prior to assigning the cultivar name.

The new *Salvia* was further evaluated and asexually propagated initially by division and later by basal cuttings taken at the same nursery in Zeeland, Michigan, USA in 2021. Evaluation of these and further cutting grown plants shows that *Salvia* 'Big Sky' continues to be stable and produce true to type plants in successive generations of asexual propagation.

SUMMARY OF THE INVENTION

Plants of *Salvia* 'Big Sky' have not been observed under all possible environmental conditions. The phenotype may vary somewhat with variations in environment such as temperature, nutrition and light intensity without, however, any variance in genotype.

The closest comparison plants known to the inventor are: 'Midnight Model' U.S. Plant Pat. No. 29,498, 'Indigo Girl' U.S. Plant Pat. No. 31,254, and 'Evening Attire' U.S. Plant Pat. No. 32,573.

'Midnight Model' has smaller flowers that are violet-blue with smaller foliage on smaller plants. 'Indigo Girl' has a smaller habit and smaller inflorescences with smaller violet-colored flowers. 'Evening Attire' has a smaller habit, smaller foliage, flower buds of dark violet-blue, and flowers that are dark violet-blue. All of these comparison varieties are smaller in habit with less branching and flower earlier in the season.

Both of the parents are much taller with larger basal foliage and the flowering period is later.

The following characteristics in combination distinguish *Saliva* 'Big Sky' as a new and distinct cultivar from all other cultivars known to the inventor:

1. Large, mounded, vigorous, and winter-hardy habit;
2. Stiff, upright, heavily-branched panicles flowering without vernalization and repeating if deadheaded;

3. Large violet-blue flowers densely arranged in verticils;
4. Large, rugose, dark-green foliage.

BRIEF DESCRIPTION OF THE DRAWINGS

The photographs of the new plant demonstrate the unique traits and the overall appearance of *Salvia* 'Big Sky'. The colors are as accurate as reasonably possible with color reproductions. Variation in ambient light spectrum, source and direction may cause the appearance of minor variation in color. The plant used in the photographs was a three-year-old plant grown in an open, full-sun trial garden at a wholesale perennial nursery in Zeeland, Michigan with supplemental water and fertilizer when needed.

DETAILED BOTANICAL DESCRIPTION

Figure 1:
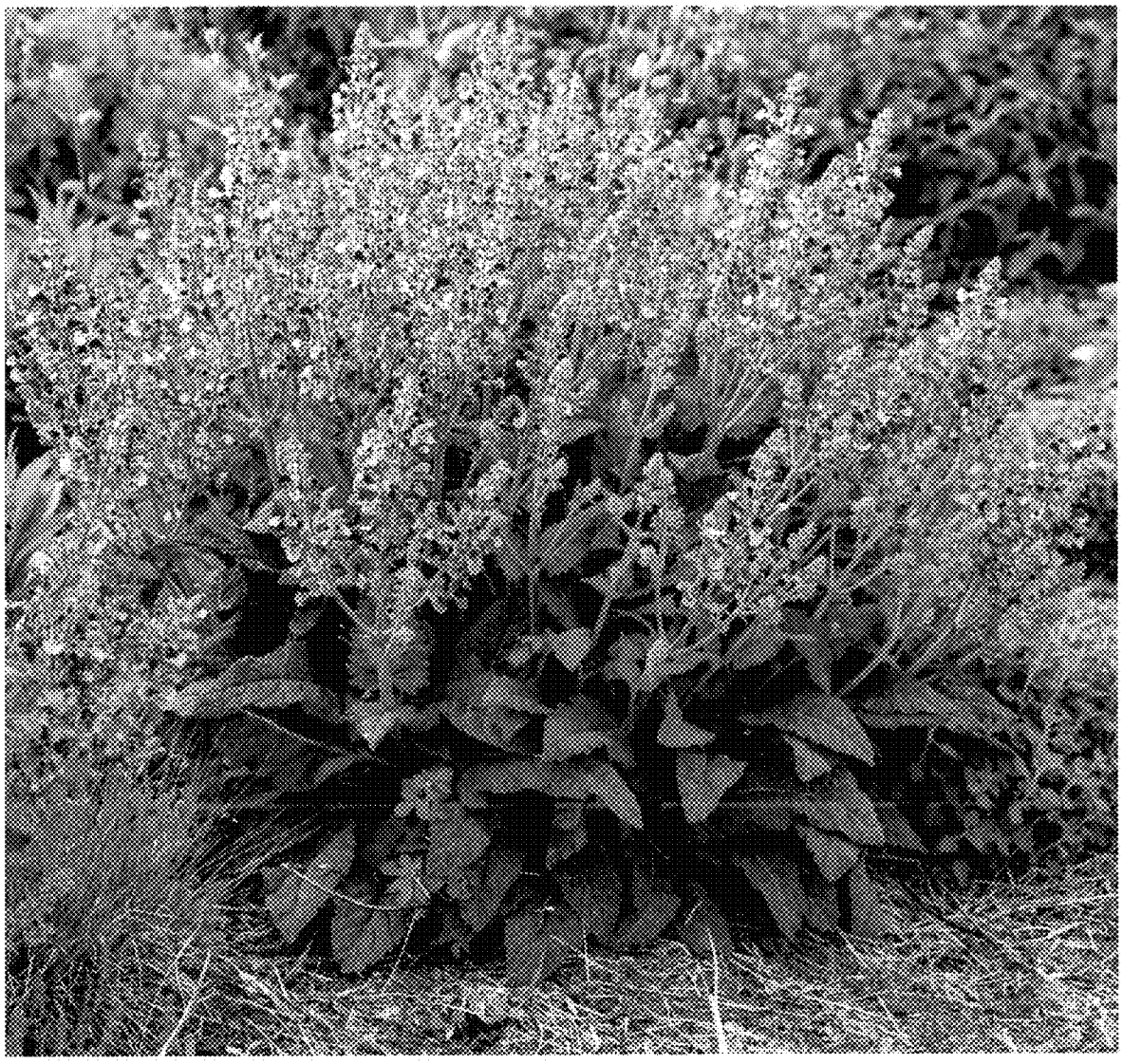
FIG. 1 shows the plant habit in full flower in a landscape.
Figure 2:
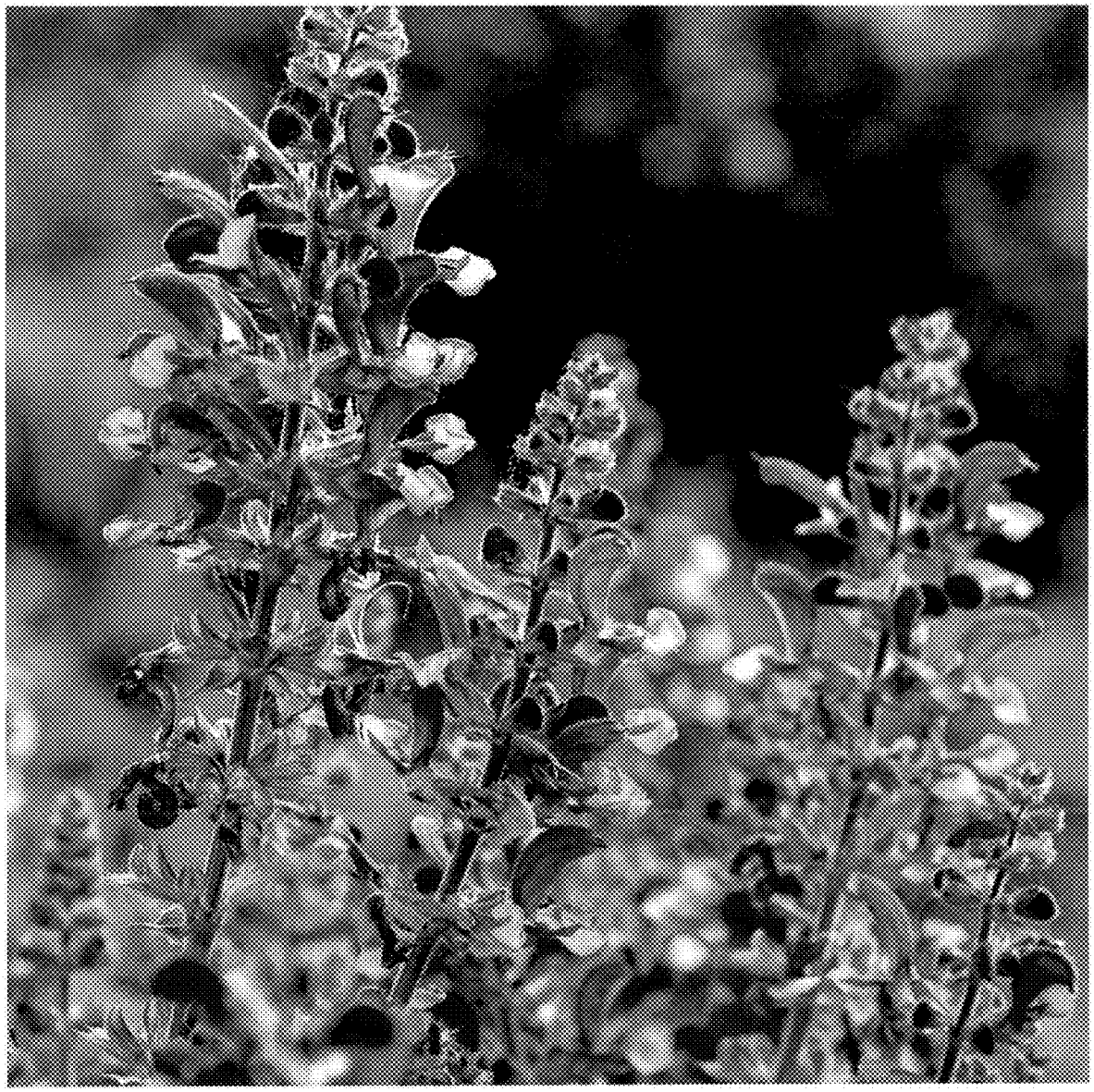
FIG. 2 shows a close-up of the flower scape with the buds, flowers, stems and calyxes.

The following descriptions and color references except where common dictionary terms are used are based on the 2015 edition of The Royal Horticultural Society Colour Chart. *Salvia* 'Big Sky' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing in an outdoor full sun trial garden at a wholesale perennial nursery in Zeeland, MI. Plants were given supplemental water and fertilizer as needed.

Botanical classification: *Salvia* hybrid;

Parentage: Female or seed parent was the proprietary hybrid 18-25-1; male or pollen parent was the proprietary hybrid 18-30-1;

Plant habit: Winter-hardy herbaceous perennial; multi-stemmed, compact, rounded, with mostly basal foliage, and flowers in several tightly arranged verticils on branched upright racemes displayed above foliage; in flower with panicles about 76 cm tall and about 80 cm wide at the fullest point about 40 cm above soil; cauline foliage extends up the stems about 44 cm; about 18 flowering panicles per plant;

Propagation: By basal vegetative shoot cuttings; time to produce a rooted stems about two weeks;

Growth rate: Rapid, vigorous, finishing in a 65 mm container in about 6 weeks from rooted cutting, and from 65 mm container to flowering 3.8-liter container in about 7 weeks;

Root description: Fine, well-branched; color dependent on age and soil type, from cream to dark tan in color depending on age and soil matrix;

Foliage: Opposite; simple; moderately rugose; lanceolate; margin irregularly crenate; adaxial surface glabrous, and abaxial micro-puberulent; acute apex and base cordate, with lobes not overlapping; leaf blades to about 24.5 cm long and 11 cm across, decreasing in size distally; average about 20 cm long and 7 cm across; between RHS 146B and RHS 144A, young abaxial surface between RHS 144A and RHS 146B; mature adaxial between NN137A and RHS NN137B, mature abaxial nearest RHS 147B;

Venation: Reticulate; impressed on adaxial side and costate on abaxial side; midrib adaxial and abaxial pubescent; adaxial secondary veins glabrous; abaxial secondary veins micro-puberulent;

Vein color: Adaxial midrib nearest RHS 145C; adaxial primary and secondary veins nearest RHS 146C; abaxial midrib nearest RHS 145C distally and nearest RHS 145D proximally; abaxial primary veins nearest RHS 145C and secondary veins nearest RHS 147C gradually darkening to nearest RHS 147B toward leaf margin;

Petiole: Slightly concavo-convex; pubescent to glandular; to about 14.5 cm long and 9 mm wide, average 6.5 cm long and 6 mm wide at base;

Petiole color: Adaxial between RHS 146D and RHS 145A with a faint blush of nearest RHS 185B in the proximal 5 mm to 15 mm; abaxial between RHS 146D and RHS 145C proximally and distally nearest 145C in the longitudinal center and between RHS 146C and RHS 146B along the margin;

Flower description: Perfect; bilabiate; zygomorphic; fused corolla portion glabrous adaxial and puberulent abaxial;

Flower size: 21 mm long to tip of exserted stigma, 9 mm tall, 4 mm wide; corolla 20 mm long, 9 mm tall, 4 mm wide; corolla fused basal portion 9 mm long, 4 mm tall and 3 mm wide;

Inflorescence: Panicle; with up to 10 branches; branched at about 45° angle; flowering portion to 32 cm long and 32 cm wide; frequently compound branched; branches to 26 cm long and 3 mm across base; verticillate with flowering generally beginning at lower verticils and advancing up the scape, but not all flowers at each verticil opening at the same time giving the effect of a scape being in continuous flower for longer periods; typically five to six flowers per verticil; average distance between verticils about 12 mm, greater proximally and less distally; about 16 verticils per main stem; about 200 to 300 flowers per panicle;

Flowering period: Flowering beginning late spring for about six weeks and repeating if initial inflorescences removed;

Peduncle: Quadrangular with longitudinal furrows on each side; pubescent to glandular; to 29 cm long and 7 mm across at base;

Peduncle color: Proximal portion between RHS 143A and RHS 144A and distal portion nearest RHS 137B in furrows with quadrangular edges nearest RHS 187A;

Flower aspect: Flower midline projected about 10-degree angle above horizontal and hood petal about 45-degree angle above horizontal;

Flower longevity: About four days on the plant or as cut flower; calyx persistent; self-cleaning, corolla, pistil, and stamen not persistent;

Flower fragrance: None detected under present growing conditions;

Flower buds one day prior to anthesis: Arcuate dorsally, flat ventrally and flattened slightly laterally; with rounded apex; pubescent; about 21 mm long to exerted stigma, 9 mm tall and 4 mm wide;

Bud color: Exposed dorsal petals blend between RHS N89C and RHS N88A and ventral petals nearest RHS 93C and fused exposed base nearest RHS N88C; abaxial calyx nearest RHS 137B distally, nearest RHS 148D proximally, dorsally moderately blushed with nearest RHS 187A to near solid RHS 187A, and veins variable, nearest RHS NN137D to solid RHS 187A;

Petals: Bilabiate corolla consisting of an upper cucullate and lower labium with three lobes;

Hood (upper) petal: Glandular abaxial, glabrous adaxial; about 25 mm long including fused base, 6 mm tall, and 2 mm across, extending 12 mm beyond fusion point; folded along longitudinal axis; apex rounded and emarginate, with 2 mm deep notched apex and base fused with labium in proximal 10 mm;

Hood color: Adaxial between RHS 93C and RHS 93D, abaxial nearest RHS 93B;

Labium (lower) petal: Consisting of three lobes, two proximal side lobes and larger center lobe;

*Center lobe*.—Obcordate, cupped; rounded emarginate apex with notch about 1.5 mm deep; margin slightly crenulate; base micro-puberulent in the distal abaxial center, glabrous adaxial and outer abaxial margin; size about 24 mm long (including fused base) extending 12 mm beyond fusion point; natural width 10 mm and when spread to 12 mm.

*Center lobe color*.—Adaxial between RHS 93C and RHS 93D, abaxial nearest RHS 93C.

*Side lobes*.—Lanceolate; apices acute; base fused to corolla tube; revolute; puberulent to glandular abaxial and glabrous adaxial; size about 4 mm long from fusion and 2 mm wide.

*Side lobes color*.—Nearest RHS 93B adaxial and nearest RHS 93C abaxial.

Androecium: Two, adnate with corolla in proximal 12 mm, contained within hood petal except when triggered by pollinator;

*Filament*.—Glabrous; fused in basal 12 mm of corolla tube; arcuate about 11 mm long around inside of hood petal; about 23 mm long and less than 0.5 mm diameter with a 2 mm long trip mechanism at base; color of filament nearest RHS 85C distally and nearest RHS 85D proximally; color of trip mechanism between RHS 85D and RHS 85C.

*Anther*.—Glabrous; oblong ellipsoidal; dorsifixed; longitudinal; about 2 mm long and 0.5 mm diameter; color nearest RHS N187A.

*Pollen*.—Rare; less than 0.1 mm; color nearest RHS 13B.

Gynoecium: One, arcuate around inside of hood petal;

*Style*.—Exserted; about 30 mm long and 0.5 mm diameter; color nearest RHS NN155D at base, transitioning distally about 6.0 mm before stigma split to between RHS N88C and RHS N88B.

*Stigma*.—Bifurcate and curved in the terminal 2 mm; about 0.3 mm diameter; apex acute; color nearest RHS N88A.

*Ovary*.—Superior; four ovules; color nearest RHS 145C.

*Fruit*.—Rare; rounded to ellipsoidal and slightly flattened; glabrous; matte surface; to about 2 mm long, 1.5 mm across, and 1 mm thick; color at maturity nearest RHS 200A.

Calyx: Campanulate; about 9 mm long and 6 mm tall at mouth and 4 mm wide; fused in basal 6 mm; lower set bifurcate in distal 3 mm; upper set trifurcate in distal 1 mm;

Sepals: Five, three upper and two lower; lanceolate; acute apex; base fused;

Sepal color: Adaxial ventral nearest RHS 148D, dorsal nearest RHS 148C and lightly to moderately blushed with nearest RHS 187A, veins nearest RHS 137C; abaxial calyx nearest RHS 137B distally, nearest RHS 148D proximally, dorsally moderately blushed with nearest RHS 187A to near solid RHS 187A, and veins variable, nearest RHS NN137D to solid RHS 187A;

Bracts: Each verticil and branch subtended by two opposite deltoid bracts; apex narrowly acute to acuminate, base sessile and truncate, margin crenate and ciliolate; glabrous adaxial and pubescent abaxial; verticil bract size up to 10 mm long and 7 mm wide, branch bract to 42 mm long and 32 mm wide; both verticil and branch bracts decreasing distally;

Bract color: Verticil bract adaxial and abaxial center portion nearest RHS 145C and margin and outer portion nearest RHS 144A; branch bract adaxial nearest between RHS 137B and RHS 137C, abaxial nearest RHS 137B;

Pedicels: Cylindrical; puberulent to glandular; to about 3.5 mm long and 1 mm diameter, average 2 mm long and 0.7 mm diameter; slightly drooping at flower anthesis;

Pedicel color: Variable; nearest RHS N79B in high light exposure, nearest RHS N148C in lower light exposure;

Culture: Plants of *Salvia* 'Big Sky' perform best with adequate moisture and good drainage and are hardy from USDA zone 3 to 8.

Disease and pest resistance: Resistant to diseases and pests beyond that common to *Salvia* has not been noted.

It is claimed:

1. The new and distinct perennial *Salvia* plant named 'Big Sky' as herein described and illustrated.

* * * * *